United States Patent [19]
Coleman

[11] Patent Number: 4,508,726
[45] Date of Patent: Apr. 2, 1985

[54] TREATMENT OF PANIC DISORDERS WITH ALPRAZOLAM

[75] Inventor: James H. Coleman, Cumberland, R.I.

[73] Assignee: The Upjohn Company, Kalamazoo, Mich.

[21] Appl. No.: 518,332

[22] Filed: Aug. 1, 1983

Related U.S. Application Data

[63] Continuation of Ser. No. 418,922, Sep. 16, 1982, abandoned.

[51] Int. Cl.³ .............................................. A61K 31/41
[52] U.S. Cl. ..................................................... 514/220
[58] Field of Search .......................................... 424/269

[56] References Cited

U.S. PATENT DOCUMENTS 3,987,052  10/1976  Hester .................................. 424/269

Primary Examiner—Stanley J. Friedman
Attorney, Agent, or Firm—William G. Jameson; John J. Killinger

[57] ABSTRACT

Therapeutic process for treating panic disorders in humans comprising, the systemic administration of a 1-methyl-6-phenyl-8-chloro-4H-s-triazolo[4,3-a][1,4]benzodiazepine including the N-oxides and pharmacologically acceptable acid addition salts thereof in combination with a pharmaceutical carrier.

3 Claims, No Drawings

TREATMENT OF PANIC DISORDERS WITH ALPRAZOLAM

This application is a continuation of Ser. No. 418,922, filed Sept. 16, 1982, now abandoned.

BRIEF SUMMARY OF THE INVENTION

This invention is a prophylatic or therapeutic process for treating panic disorders in humans comprising the systemic administration of a benzodiazepine of the Formula 1:

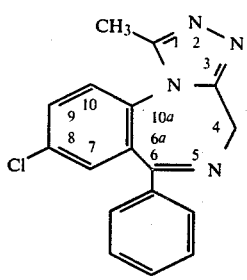

Formula 1 and including the N-oxides and pharmacologically acceptable acid addition salts thereof in combination with a pharmaceutical carrier.

BACKGROUND OF THE INVENTION

Panic attacks, a spontaneous attack, thought to be a biochemical disorder of genetic origin, begins in the majority of subjects at ages 15 to 30 years. The attacks occur with no apparent reason to the subject and are accompanied by symptoms of hyperventilation, heart-pounding, pain in head, numbness or tingling of the limbs, hot and cold flashes, lump in throat, and the like. The attacks continue to occur and can lead the subject to become house bound.

Various treatments have been prescribed, including hypnosis and behavior therapies and chemotherapy, particulary the administration of imipramine hydrochloride or phenalzine sulfate. The latter although somewhat effective have undesirable side-effects, chlordiazepoxide and diazepam have been tried but found not effective to block the panic attack.

Alprazolam has been indicated for the management of anxiety disorders.

DETAILED DESCRIPTION

The compounds of the Formula I can be prepared by methods disclosed in U.S. Pat. No. 3,987,052, issued Oct. 19, 1976 and as disclosed hereafter.

The oxidation of a compound of the Formula I normally follows a 2-step process with the formation of an oxazirino structure.

The (5) N-oxides of a compound of the Formula I can also be made by reacting a 2-methoxy-5-phenyl-7-chloro-3H-1,4-benzodiazepine 4-oxide with acethydrazide. This reaction can be carried out in a solvent inert to the reaction such as a lower alkanol of boiling range of about 100° C. or above, especially 1-butanol or 1-pentanol. It is convenient to reflux the reaction mixture, and a convenient reaction temperature is in the range of 100°-140° C. Under these conditions, the reaction time will be from 12 to 48 hours.

The peracid oxidation method described above for producing the (5) N-oxides of a compound of the Formula I produces an intermediate oxazirino compound as described above, and this latter compound can be further rearranged to the desired (5) N-oxide by heating in an appropriate solvent inert to the reaction and capable of being sustained in liquid form at normal pressure at temperatures of 150°-200° C. Suitable reaction solvents are the liquid paraffinic hydrocarbons of 10-18 carbon atoms or other solvent hydrocarbons boiling above about 150° C. such as mesitylene. The reaction is conveniently carried out under reflux for 10 minutes to 1 hour.

Acid addition salts of compounds of the Formula I can be prepared by neutralization of the free base with the appropriate amount of an inorganic or organic acid, examples of which are hydrochloric, hydrobromic, sulfuric, nitric, phosphoric, acetic, lactic, benzoic, salicyclic, glycolic, succinic, tartaric, maleic, malic, pamoic, cyclohexanesulfamic, citric and methanesulfonic acids, and like acids. The neutralization can be carried out by a variety of procedures known to the art to be generally useful for the preparation of amine acid addition salts. The choice of the most suitable procedure will depend on a variety of factors including convenience of operation, economic consideration, and particularly the solubility characteristics of the particular free base, the acid, and the acid addition salt. If the acid is soluble in water, the free base can be dissolved in water containing an equivalent amount of the acid, and thereafter, the water can be removed by evaporation; in some instances, the salt precipitates from the aqueous solution, particularly when cooled, and evaporation is not necessary. If the acid is soluble in a relatively nonpolar solvent, for example, diethyl ether or diisopropyl ether, separate solutions of acid and free base in such a solvent can be mixed in equivalent amounts, whereupon the acid addition salt will usually precipitate because of its relatively low solubility in the nonpolar solvent. Alternatively, the free base can be mixed with an equivalent amount of the acid in the presence of a solvent of moderate polarity, for example, a lower alkanol, a lower alkanone, or a loweralkyl ester of a lower alkanoic acid. Examples of these solvents are ethanol, acetone, and ethyl acetate, respectively. Subsequent admixture of the resulting solution of acid addition salt with a solvent of relatively low polarity, for example, diethyl ether or hexane, will usually cause precipitation of the acid addition salt. These acid addition salts are useful for upgrading the free bases.

The compositions of the present invention are presented for administration to humans in unit dosage forms, such as tablets, capsules, pills, powders, granules, sterile parenteral solutions or suspensions, and oral solutions or suspensions, and oil in water and water in oil emulsions containing suitable quantities of the compound of Formula I.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are parpared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term unit dosage form as used in the specification and claims refers to physically discrete units suitable as unitary dosages for human subjects and animals, each unit containing a predetermined quantity of a active material calculated to prevent panic attacks or treat panic disorders in association with the required pharmaceutical diluent, carrier or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segregated multiples of any of the foregoing, and other forms as herein described.

The dosage of the compound for treatment depends on route of administration; the age, weight, and condition of the patient. A dosage schedule of from about 1 to 10 mg/day in a single or divided dose, embraces the effective range for treating panic disorders for which the compositions are effective. The dosage to be administered is calculated on the basis of from about 0.01 to about 0.4 mg/kg by weight of subject per day.

The compound is compounded with a suitable pharmaceutical carrier in unit dosage form for convenient and effective administration. In the preferred embodiments of this invention, the dosage units contain the compound in: 0.1, 0.5, 1 and 10 mg amount for systemic treatment; and 0.1% to 1% w/v for parenteral treatment.

The compositions are useful in preventing and treating panic attacks in adults (age fifteen years or more), agaraphobia, and phobic anxiety.

The following examples are illustrative of the best mode contemplated by the inventor for carrying out his invention and are not to be construed as limiting.

EXAMPLE 1

A lot of 10,000 tablets, each containing 0.5 mg of 8-chloro-1-methyl-6-phenyl-4H-s-triazolo[4,3-a][1,4]benzodiazepine is prepared from the following types and amounts of ingredients:

| | |
|---|---:|
| 8-Chloro-1-methyl-6-phenyl-4H—s-triazolo-[4,3-a][1,4]benzodiazepine | 1 Gm |
| Dicalcium phosphate | 1,500 Gm |
| Methylcellulose, U.S.P. (15 cps.) | 60 Gm |
| Talc | 150 Gm |
| Corn Starch | 200 Gm |
| Calcium stearate | 12 Gm |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in preventing panic attcks at a dose of 1 tablet 4 times a day.

EXAMPLE 2

One thousand two-piece hard gelatin capsules, each containing 0.5 mg of 8-chloro-1-methyl-6-phenyl-4H-s-triazolo[4,3-a][1,4]benzodiazepine are prepared from the following types and amounts of ingredients:

| | |
|---|---:|
| 8-Chloro-1-methyl-6-phenyl-4H—s-triazolo[4,3-a][1,4]benzodiazepine | 0.5 Gm |
| Talc | 25 Gm |
| Magnesium stearate | 250 Gm |

The ingredients are mixed well and filled into capsules of the proper size.

Capsules so prepared are useful to prevent panic attacks at a dose of one capsule four times a day.

EXAMPLE 3

One thousand tablets for sublinqual use are prepared from the following ingredients:

| | |
|---|---:|
| 8-Chloro-1-methyl-6-phenyl-4H—s-triazolo[4,3-a][1,4]benzodiazepine | 1 Gm |
| Polyethylene glycol 4,000, powdered | 150 Gm |
| Polyethylene glycol 6,000, powdered | 75 Gm |

The ingredients are mixed well and compressed into sublingual-type tablets weighing 226 mg.

These tablets placed under the tongue are useful in treating panic attacks at a dose of 1 tablet.

EXAMPLE 4

Soft gelatin capsules for oral use, each containing 10 mg of 1-methyl-6-phenyl-4H-s-triazolo[4,3-a][1,4]benzodiazepine are prepared by first dispersing the micronized compound in corn oil to render the material capsulatable and then encapsulating in the usual manner.

One capsule taken daily is useful to prevent panic attacks.

EXAMPLE 5

One thousand tablets, each containing 5 mg. of 8-chloro-1-methyl-6phenyl-4H-s-triazolo[4,3-a][1,4]benzodiazepine are made from the following types and amounts of ingredients:

| 8-Chloro-1-methyl-6-phenyl-4H—s-triazolo [4,3-a][1,4]benzodiazepine | 5 Gm |
| --- | --- |
| Lactose | 355 Gm |
| Microcrystalline cellulose NF | 120 Gm |
| Starch | 16 Gm |
| Magnesium stearate powder | 4 Gm |

The ingredients are screened and blended together and pressed into 500 mg tablets.

The tablets are useful to prevent panic attacks at a dose of one tablet twice a day.

EXAMPLE 6

A sterile preparation suitable for intramuscular injection and containing 1 mg of 8-chloro-1-methyl-6-phenyl-4H-s-triazolo[4,3-a][1,4]benzodiazepine in each milliliter is prepared from the following ingredients:

| 8-Chloro-1-methyl-6-phenyl-4H—s-triazolo [4,3-a][1,4]benzodiazepine | 1 Gm |
| --- | --- |
| Benzyl benzoate | 200 ml |
| Methylparaben | 1.5 Gm |
| Propylparaben | 0.5 Gm |
| Cottonseed oil, q.s. | 1,000 ml |

One milliliter of this sterile preparation is injected to treat panic attack.

EXAMPLE 7

Following the procedure of the preceding Example 1 to 6, inclusive, compositions are similarly prepared and administered substituting one equal amount of the N-oxide or hydrochloride salt of the active compound of the example.

I claim:

1. A process for preventing or treating panic attacks comprising the administration to a human subject susceptible to panic attacks, in unit dosage form, from about 0.01 mg to about 0.4 mg/kg body weight of 8-chloro-1-methyl-6-phenyl-4H-s-triazolo[4,3-a][1,4]benzodiazepine or the pharmacologically acceptable acid addition salt or a (5) N-oxide thereof in association with a pharmaceutical carrier.

2. The process of claim 1 wherein the 8-chloro-1-methyl-6-phenyl-4H-s-triazolo[4,3-a][1,4]benzodiazepine is in the form of the (5) N-oxide.

3. The process of claim 1 wherein the 8-chloro-1-methyl-6-phenyl-4H-s-triazolo[4,3-a][1,4]benzodiazepine is in the form of the free base.

* * * * *

UNITED STATES PATENT OFFICE
CERTIFICATE OF CORRECTION

Patent No. 4,508,726      Dated April 2, 1985

Inventor(s) James H. Coleman

It is certified that error appears in the above-identified patent and that said Letters Patent are hereby corrected as shown below:

On the title page "3 Claims" should read -- 10 Claims --.

Column 4, line 8: "agaraphobia" should read -- agoraphobia --.

Column 6, lines 19-21 (Claim 1): "A process for preventing panic attacks comprising the administration to a human subject susceptible to panic attacks," should read -- A process for preventing or treating panic attacks comprising the administration to a human subject in need of such treatment, --.

Column 6: The following claims should appear in the printed patent:

"4. A process for preventing recurrent panic attacks comprising the administration to a human subject in need of such treatment, in unit dosage form, from about 0.01 mg to about 0.4 mg/kg body weight of 8-chloro-1-methyl-6-phenyl-4H-s-triazolo[4,3-a]benzodiazepine or the pharmacologically acceptable acid addition salt or a (5) N-oxide thereof in association with a pharmaceutical carrier."

"5. The process of claim 4 wherein the 8-chloro-1-methyl-6-phenyl-4H-s-triazolo[4,3-a][1,4]benzodiazepine is in the form of the (5) N-oxide."

"6. The process of claim 4 wherein the 8-chloro-1-methyl-6-phenyl-4H-s-triazolo[4,3-a][1,4]benzodiazepine is in the form of the free base."

"7. A process for treating panic disorders comprising the administration to a human subject in need of such treatment, in unit dosage form, from about 0.1 mg to about 0.4 mg/kg body weight of 8-chloro-1-methyl-6-phenyl-4H-s-triazolo[4,3-a][1,4]benzodiazepine or the pharmacologically acceptable acid addition salt or a (5) N-oxide thereof in association with a pharmaceutical carrier."

"8. The process of claim 7 wherein the 8-chloro-1-methyl-6-phenyl-4H-s-triazolo[4,3-a][1,4]benzodiazepine is in the form of the (5) N-oxide."

"9. The process of claim 7 wherein the 8-chloro-1-methyl-6-phenyl-4H-s-triazolo[4,3-a][1,4]benzodiazepine is in the form of the free base."

UNITED STATES PATENT OFFICE
CERTIFICATE OF CORRECTION

Patent No. 4,508,726    Dated    April 2, 1985

Inventor(s) James H. Coleman

It is certified that error appears in the above-identified patent and that said Letters Patent are hereby corrected as shown below:

"10. The process of claim 1 wherein the panic attacks are in patients with agoraphobia."

Signed and Sealed this

Twenty-second Day of October 1985

[SEAL]

Attest:

Attesting Officer

DONALD J. QUIGG

Commissioner of Patents and Trademarks—Designate